(12) United States Patent
Maeda et al.

(10) Patent No.: US 11,752,279 B2
(45) Date of Patent: Sep. 12, 2023

(54) ULTRASONIC VIBRATOR DRIVING APPARATUS AND MESH NEBULIZER

(71) Applicant: OMRON HEALTHCARE CO., LTD., Muko (JP)

(72) Inventors: Masao Maeda, Kyoto (JP); Hidetaka Togo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 1217 days.

(21) Appl. No.: 16/352,890

(22) Filed: Mar. 14, 2019

(65) Prior Publication Data

US 2019/0209790 A1 Jul. 11, 2019

Related U.S. Application Data

(63) Continuation of application No. PCT/JP2017/028911, filed on Aug. 9, 2017.

(30) Foreign Application Priority Data

Sep. 27, 2016 (JP) .................................. 2016-188716

(51) Int. Cl.
*A61M 11/00* (2006.01)
*B05B 17/06* (2006.01)
(Continued)

(52) U.S. Cl.
CPC ....... *A61M 11/005* (2013.01); *B05B 17/0623* (2013.01); *B06B 1/0284* (2013.01);
(Continued)

(58) Field of Classification Search
CPC ................ A61M 1/005; A61M 15/001; A61M 15/0085; B05B 17/06; B05B 17/0623;
(Continued)

(56) References Cited

U.S. PATENT DOCUMENTS

2006/0243277 A1  11/2006  Denyer et al.
2008/0088202 A1   4/2008  Duru
2015/0202387 A1*  7/2015  Yu ........................ A61M 11/005
                                                    128/200.16

FOREIGN PATENT DOCUMENTS

FR    2 903 331 A1   1/2008
JP    64-67286 A     3/1989
(Continued)

OTHER PUBLICATIONS

Machine Translation of DESCRIPTION_WO2009096346A1_07/12/2023 (Year: 2009).*

(Continued)

*Primary Examiner* — Kendra D Carter
*Assistant Examiner* — Mautin I Ashimiu
(74) *Attorney, Agent, or Firm* — KEATING AND BENNETT, LLP

(57) ABSTRACT

An ultrasonic vibrator driving apparatus performs driving by applying an alternating voltage as a drive voltage to an ultrasonic vibrator that includes a piezoelectric element and has a unique resonance frequency. The drive voltage is generated with a variable frequency in a frequency range including the resonance frequency of the ultrasonic vibrator. The frequency of the drive voltage is repeatedly swept with a predetermined sweep width and a predetermined sweep period so as to include the resonance frequency, based on a reference frequency set according to the resonance frequency of the ultrasonic vibrator. The sweep period and the sweep width are restricted by being associated so as to fall within a predetermined allowed range on a two-dimensional map divided by the sweep period and the sweep width.

7 Claims, 6 Drawing Sheets

(51) Int. Cl.
*B06B 1/02* (2006.01)
*B06B 1/06* (2006.01)
*B06B 3/00* (2006.01)
*A61M 15/00* (2006.01)
*B05B 17/00* (2006.01)
*B06B 3/02* (2006.01)

(52) U.S. Cl.
CPC .............. *B06B 1/06* (2013.01); *B06B 3/00* (2013.01); *B06B 2201/76* (2013.01); *B06B 2201/77* (2013.01)

(58) Field of Classification Search
CPC ............ B05B 17/0638; B05B 17/0653; B05B 17/0669; B05B 17/00–0692
See application file for complete search history.

(56) References Cited

FOREIGN PATENT DOCUMENTS

| | | | |
|---|---|---|---|
| JP | 1-164104 A | 6/1989 | |
| JP | 2005-261520 A | 9/2005 | |
| JP | 2006-181496 A | 7/2006 | |
| JP | 2009-165947 A | 7/2009 | |
| WO | WO-2009096346 A1 * | 8/2009 | ......... B05B 17/0623 |

OTHER PUBLICATIONS

Official Communication issued in German Patent Application No. 11 2017 004 839.7, dated Apr. 22, 2020.
Official Communication issued in International Patent Application No. PCT/JP2017/028911, dated Oct. 31, 2017.

* cited by examiner

| SWEEP WIDTH | SWEEP PERIOD | | | | |
|---|---|---|---|---|---|
| | | 0.05msec | 0.1msec | 1sec | 10sec |
| | fo±0.75kHz | ○ | × | × | × |
| | fo±0.5kHz | ○ | ○ | × | × |
| | fo±0.25kHz | ○ | ○ | ○ | × |
| | fo±0.1kHz | ○ | ○ | ○ | ○ |
| | fo−0.25kHz~fo+0.1kHz | ○ | ○ | ○ | ○ |

ULTRASONIC VIBRATOR DRIVING APPARATUS AND MESH NEBULIZER

CROSS REFERENCE TO RELATED APPLICATIONS

This application claims the benefit of priority to Japanese Patent Application No. 2016-188716 filed on Sep. 27, 2016 and is a Continuation Application of PCT Application No. PCT/JP2017/028911 filed on Aug. 9, 2017. The entire contents of each application are hereby incorporated herein by reference.

BACKGROUND OF THE INVENTION

1. Field of the Invention

The present invention relates to an ultrasonic vibrator driving apparatus, and more specifically relates to an ultrasonic vibrator driving apparatus that drives an ultrasonic vibrator having a unique resonance frequency by applying a drive voltage (alternating voltage) thereto. Also, the present invention relates to a mesh nebulizer including such an ultrasonic vibrator driving apparatus.

2. Description of the Related Art

Conventionally, for example, JP 2006-181496A has disclosed, as a type of ultrasonic vibrator driving apparatus, an ultrasonic vibrator driving apparatus that can vary (sweep) the frequency of the driving voltage over time such that the resonance frequency of the ultrasonic vibrator is passed, in order to reduce the power consumption.

Also, JP 2005-261520A discloses that a section that sufficiently includes the minimum value and the maximum value of the resonance frequency of the ultrasonic vibrator is used as the sweep range in order to make the frequency of the drive voltage non-adjustable in the case of driving multiple ultrasonic vibrators.

Incidentally, if the above-described ultrasonic vibrator is of a type in which a piezoelectric element and a horn that transmits the vibration of the piezoelectric element are integrally combined (referred to as a "horn vibrator" as appropriate), as is widely used in order to form a mesh nebulizer, for example, the Q value (sharpness of resonance) is extremely high, as can be understood from FIG. 8. For this reason, as shown in FIG. 9, regarding a certain horn vibrator (the unique resonance frequency is denoted as "fr"; the units of fr are kHz), the practical range of frequencies of the driving voltage is limited to the range $\Delta f$ from (fr−0.8 kHz) to fr. Note that in FIGS. 8 and 9, the horizontal axis indicates the frequency of the drive voltage and the vertical axis indicates the impedance (indicated by the solid line) and the phase (indicated by the broken line) of the horn vibrator. As a result, as described in JP 2006-181496A and JP 2005-261520A, when the frequency of the drive voltage is simply swept over time such that the resonance frequency of the horn vibrator is passed, there is a problem in that the driving efficiency of the horn vibrator decreases.

Furthermore, it is known that there is a manufacturing variation of about ±1.5 kHz in the resonance frequency fr of the horn vibrator. FIG. 10 shows changes in spray amount per unit time when the frequency of a drive voltage composed of a square wave is changed, for three samples, namely samples No. 1 to 3, which have different resonant frequencies due to manufacturing variation. If the frequency of the drive voltage exceeds the resonance frequency fr1=178.85 kHz in Sample No. 1, the resonance frequency fr2=179.15 kHz in Sample No. 2, and the resonance frequency fr3=179.40 kHz in Sample No. 3, each by about 0.03 kHz at most, the spray amount per unit time decreases by about half. In this manner, the frequency of the drive voltage exceeds the resonance frequency of the horn vibrator due to the manufacturing variation in the resonance frequency fr, and as a result, there is also a possibility that the driving efficiency will decrease.

Also, as illustrated in FIG. 11, the resonance frequency fr of the horn vibrator changes also due to the ambient temperature. FIG. 11 shows changes in the resonance frequency accompanying changes in the ambient temperature (temperature dependency) for four types of samples with different resonant frequencies. If the temperature of the horn vibrator increases, the resonance frequency fr of the horn vibrator decreases, whereas if the temperature of the horn vibrator decreases, the resonance frequency fr of the horn vibrator increases.

SUMMARY OF THE INVENTION

In view of this, preferred embodiments of the present invention provide ultrasonic vibrator driving apparatuses that each stably drive an ultrasonic vibrator having a manufacturing variation and temperature dependency of a resonance frequency, while suppressing or preventing a reduction of the driving efficiency. Also, preferred embodiments of the present invention provide mesh nebulizers each including such an ultrasonic vibrator driving apparatus.

An ultrasonic vibrator driving apparatus according to a preferred embodiment of the present invention applies an alternating voltage as a drive voltage to an ultrasonic vibrator that includes a piezoelectric element and has a unique resonance frequency, the ultrasonic vibrator driving apparatus including a drive voltage generator to generate the drive voltage with a variable frequency in a frequency range including the resonance frequency of the ultrasonic vibrator, and a sweep controller to repeatedly sweep the frequency of the drive voltage with a predetermined sweep width and a predetermined sweep period so as to include the resonance frequency, based on a reference frequency set according to the resonance frequency of the ultrasonic vibrator, and to associate and restrict the sweep period and the sweep width such that the sweep period and the sweep width fall within a predetermined allowed region on a two-dimensional map divided by the sweep period and the sweep width.

Here, the "ultrasonic vibrator" preferably includes a piezoelectric element. Thus, typically, when the frequency of the drive voltage is slightly less than the resonance frequency of the ultrasonic vibrator, the ultrasonic vibrator vibrates efficiently, whereas if the frequency of the drive voltage slightly exceeds the resonance frequency of the ultrasonic vibrator, the ultrasonic vibrator substantially stops vibrating. Also, if the temperature of the ultrasonic vibrator and its surroundings increases, the resonance frequency of the ultrasonic vibrator decreases, whereas if the temperature of the ultrasonic vibrator and its surroundings decreases, the resonance frequency of the ultrasonic vibrator increases.

Also, the "two-dimensional map" may be a two-dimensional table divided into multiple sweep periods and sweep widths, for example. Also, in the "two-dimensional map", a two-dimensional graph may be provided in which the divisions of the sweep periods and the sweep widths are very narrow and the boundary between the allowed region and the non-allowed region is substantially smooth.

With an ultrasonic vibrator driving apparatus according to a preferred embodiment of the present invention, the drive voltage generator generates the drive voltage (alternating voltage) with a variable frequency in the frequency range including the resonance frequency of the ultrasonic vibrator. The sweep controller repeatedly sweeps the frequency of the drive voltage with the predetermined sweep width and the predetermined sweep period so as to include the resonance frequency, based on the reference frequency set according to the resonance frequency of the ultrasonic vibrator. For example, at the time of starting driving, when the frequency of the drive voltage is slightly lower (e.g., about 0.2 kHz) than the resonance frequency of the ultrasonic vibrator, the ultrasonic vibrator vibrates efficiently. Accordingly, the temperature of the ultrasonic vibrator and its surroundings increases. If the temperature of the ultrasonic vibrator and its surroundings increases, the resonance frequency of the ultrasonic vibrator decreases. Accordingly, compared to the state at the time of starting driving, the period for which the frequency of the drive voltage exceeds the resonance frequency of the ultrasonic vibrator in the sweep period becomes longer, and the period for which the ultrasonic vibrator substantially does not vibrate in the sweep period becomes longer. Accordingly, the temperature of the ultrasonic vibrator and its surroundings decreases. Also, if the temperature of the ultrasonic vibrator and its surroundings decreases, the resonance frequency of the ultrasonic vibrator increases. Accordingly, compared to the immediately previous state, the period for which the frequency of the driving voltage is less than the resonance frequency of the ultrasonic vibrator in the sweep period becomes longer, and the period for which the ultrasonic vibrator efficiently vibrates in the sweep period becomes longer. Accordingly, the temperature of the ultrasonic vibrator and its surroundings once again increases. In this manner, the temperature change of the ultrasonic vibrator and its surroundings is substantially feedback-controlled and suppressed or prevented. As a result, regardless of the temperature dependency of the resonance frequency of the ultrasonic vibrator, the ultrasonic vibrator is driven stably. Also, since the sweeping is performed based on the reference frequency set according to the resonance frequency of the ultrasonic vibrator, the ultrasonic vibrator is driven stably, regardless of the manufacturing variation of the resonance frequency of the ultrasonic vibrator.

Furthermore, the sweep controller associates and restricts the sweep period and the sweep width such that they fall within an allowed range determined in advance in the two-dimensional map divided by the sweep periods and the sweep widths. Accordingly, reduction of the driving efficiency is suppressed or prevented.

An ultrasonic vibrator driving apparatus of a preferred embodiment of the present invention includes a reference frequency setter to search for and obtain the resonance frequency of the ultrasonic vibrator by sweeping the frequency of the drive voltage before the start of operation of the ultrasonic vibrator, and to set the reference frequency according to the obtained resonance frequency.

Here, setting the reference frequency "according to" a determined resonance frequency typically means setting the reference frequency so as to match the resonance frequency. However, the reference frequency may also be set slightly (e.g., about 0.2 kHz) lower than the obtained resonance frequency.

With the ultrasonic vibrator driving apparatus of this preferred embodiment, the reference frequency setter searches for and obtains the resonance frequency by sweeping the frequency of the driving voltage before the start of driving of the ultrasonic vibrator, and sets the reference frequency according to the obtained resonance frequency. Accordingly, even if the resonance frequencies of the individual ultrasonic vibrators are different due to the manufacturing variation and the temperature dependency of the ultrasonic vibrator, the reference frequency is able to be set appropriately according to the resonance frequencies of the individual ultrasonic vibrators.

With an ultrasonic vibrator driving apparatus of a preferred embodiment of the present invention, the ultrasonic vibrator is a horn vibrator including an integrated piezoelectric element and a horn to transmit vibration of the piezoelectric element.

In general, the horn vibrator has a very high Q value (sharpness of resonance) compared to a type with no horn. With the ultrasonic vibrator driving apparatus of this preferred embodiment, the ultrasonic vibrator is a horn vibrator including an integrated structure including the piezoelectric element and a horn for transmitting vibration of the piezoelectric element. Accordingly, there is a large advantage achieved by this preferred embodiment of the present invention, according to which the horn vibrator is able to be driven stably regardless of the manufacturing variation and the temperature variation of the resonance frequency.

With an ultrasonic vibrator driving apparatus of a preferred embodiment of the present invention, the vibration of the ultrasonic vibrator is used to nebulize and spray a medicinal liquid, and the allowed region on the two-dimensional map is set such that a spray amount of the medicinal liquid is about 90% or more of a spray amount achieved when the ultrasonic vibrator is vibrated at the resonance frequency.

With the ultrasonic vibrator driving apparatus of this preferred embodiment, the vibration of the ultrasonic vibrator is used to nebulize and spray a medicinal liquid. Here, the allowed region on the two-dimensional map is set such that a spray amount of the medicinal liquid is about 90% or more of a spray amount achieved when the ultrasonic vibrator is vibrated at the resonance frequency. Accordingly, reduction of the driving efficiency of the ultrasonic vibrator is reliably suppressed or prevented.

With an ultrasonic vibrator driving apparatus of a preferred embodiment of the present invention, the sweep controller sets the sweep width for sweeping toward the side of exceeding the reference frequency to be smaller than the sweep width for sweeping toward the side of being less than the reference frequency, while keeping the sweep period constant.

With the ultrasonic vibrator driving apparatus of this preferred embodiment, the sweep period is kept constant while the sweep controller sets the sweep width for sweeping to the side of exceeding the reference frequency to be smaller than the sweep width for sweeping to the side of being less than the reference frequency. Accordingly, the period in which the ultrasonic vibrator substantially does not vibrate in the sweep period becomes shorter than the period in which the ultrasonic vibrator effectively vibrates. Accordingly, reduction of the driving efficiency of the ultrasonic vibrator is furthermore suppressed or prevented.

With an ultrasonic vibrator driving apparatus of a preferred embodiment of the present invention, the sweep controller sets the sweep width for sweeping toward the side of exceeding the reference frequency to about 0.10 kHz and the sweep width for sweeping toward the side of being less than the reference frequency to about 0.25 kHz, while keeping the sweep period constant.

With the ultrasonic vibrator driving apparatus of this preferred embodiment, the sweep controller sets the sweep width for sweeping toward the side of exceeding the reference frequency to about 0.10 kHz and the sweep width for sweeping toward the side of being less than the reference frequency to about 0.25 kHz, while keeping the sweep period constant. According to a result of an experiment (described later) performed by the inventor of preferred embodiments of the present invention, and the like, this reliably suppresses or prevents reduction of the driving efficiency of the ultrasonic vibrator. For example, if the vibration of the ultrasonic vibrator is used to nebulize and spray a liquid, even if the sweep period is set to be long, such as 10 seconds, the spray amount of the liquid will be about 90% or more of the spray amount achieved when the ultrasonic vibrator is vibrated at the resonance frequency.

In another aspect, a mesh nebulizer according to a preferred embodiment of the present invention includes an ultrasonic vibrator driving apparatus according to one of the above-described preferred embodiments of the present invention, the ultrasonic vibrator being a horn vibrator including an integral structure that includes a piezoelectric element and a horn to transmit vibration of the piezoelectric element, and a flat plate-shaped or sheet-shaped mesh portion facing a vibration surface of the horn vibrator, wherein a medicinal liquid supplied between the vibration surface and the mesh portion is nebulized and sprayed through the mesh portion.

In the present specification, the "flat plate-shaped or sheet-shaped mesh portion" means an element that has multiple through holes that penetrate through a flat plate or a sheet and is structured to nebulize a liquid by passing the liquid through the through holes. Note that "sheet" encompasses a film.

According to a mesh nebulizer according to a preferred embodiment of the present invention, the liquid is able to be efficiently nebulized and sprayed.

As is evident from the description above, according to the ultrasonic vibrator driving apparatuses of preferred embodiments of the present invention, the ultrasonic vibrators having the manufacturing variation and temperature dependency of the resonance frequency are able to be driven stably while suppressing reduction of the driving efficiency. Also, according to the mesh nebulizers of various preferred embodiments of the present invention, the liquid is able to be efficiently nebulized and sprayed.

The above and other elements, features, steps, characteristics and advantages of the present invention will become more apparent from the following detailed description of the preferred embodiments with reference to the attached drawings.

Figure 1:
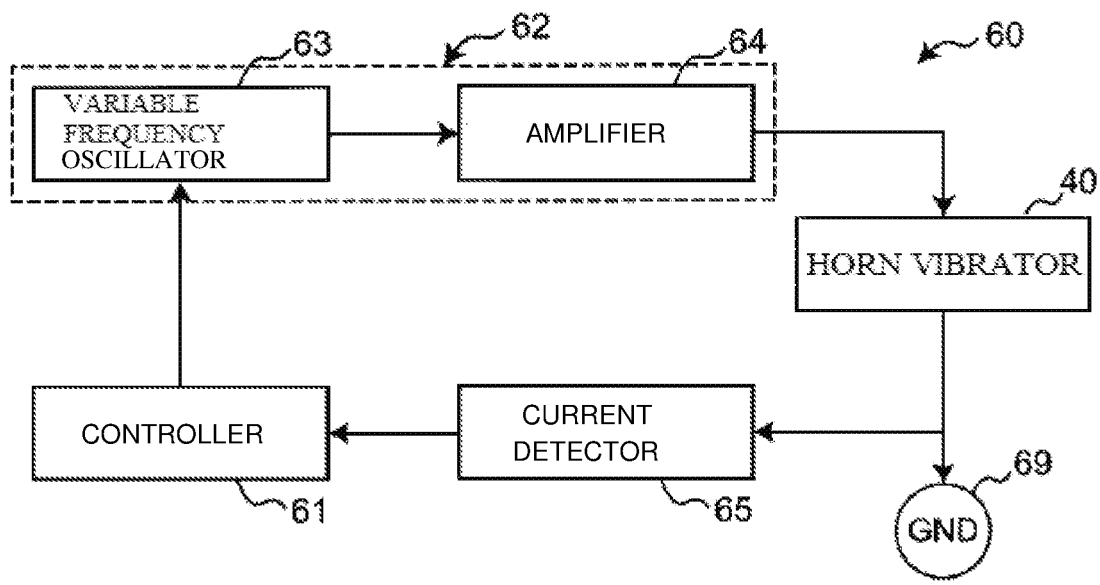
FIG. 1 is a diagram showing a block configuration of an ultrasonic vibrator driving apparatus of a preferred embodiment of the present invention.
Figure 2:
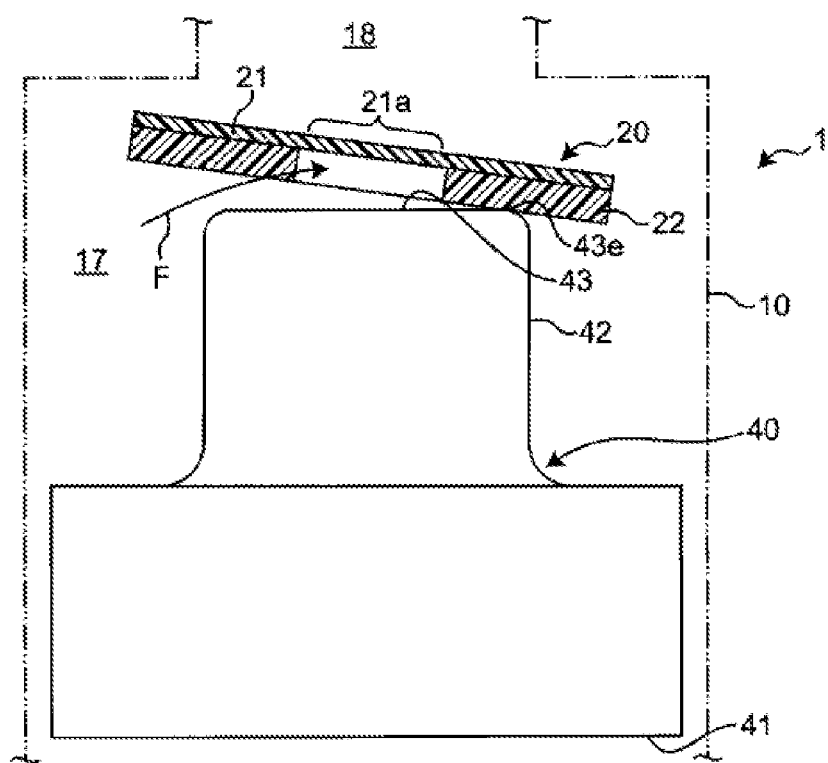
FIG. 2 is a diagram showing a configuration of a nebulization unit of a mesh nebulizer in which the ultrasonic vibrator driving apparatus is mounted.

FIG. 9 is a diagram showing a practical range of frequencies of the drive voltage for a certain horn vibrator (resonance frequency is denoted by "fr").

FIG. 10 is a diagram showing changes in spray amount per unit time when the frequency of the drive voltage is changed, for three horn vibrator samples whose resonance frequencies differ due to manufacturing variations.

FIG. 11 is a diagram showing changes in the resonance frequency accompanying changes in the ambient temperature (temperature dependency) for four horn vibrator samples with different resonance frequencies.

DETAILED DESCRIPTION OF THE PREFERRED EMBODIMENTS

Hereinafter, preferred embodiments of the present invention will be described in detail with reference to the drawings.

FIG. 2 shows a configuration of a nebulization unit of a mesh nebulizer (indicated overall by the reference numeral 1) in which an ultrasonic vibrator driving apparatus 1 of a preferred embodiment of the present invention is mounted. The mesh nebulizer 1 includes a main body 10 that includes an opening 18 in its upper portion, and a horn vibrator 40 defining and functioning as an ultrasonic vibrator built into the main body 10. A power source switch (not shown) is provided on the outer surface of the main body 10.

The horn vibrator 40 is preferably defined by an integrated structure including a vibration surface 43 horizontally opposing the opening 18 arranged thereabove, a piezoelectric element 41 arranged at a position separated downward from the vibration surface 43, and a horn 42 that is located between the piezoelectric element 41 and the vibration surface 43 and amplifies and transmits the vibration of the piezoelectric element 41 to the vibration surface 43. The drive voltage for the horn vibrator 40 (more accurately, the piezoelectric element 41) is supplied by a later-described ultrasonic vibrator driving apparatus 60. The horn vibrator 40 has a unique resonance frequency fr, as illustrated in FIGS. 8 and 9.

A replacement member 20 is arranged by being detachably mounted between the opening 18 and the vibration surface 43. The replacement member 20 includes a film 21 defining and functioning as a flat sheet that opposes the vibration surface 43, and an approximately circular ring-shaped bottom plate portion 22 that supports the circumferential edge of the film 21. The film 21 is attached through adhesion or welding to the upper surface of the bottom plate portion 22. An approximately central region of the film 21 is a mesh portion 21a. Many minute through holes (not shown) that penetrate through the film 21 are provided in the mesh portion 21a. The bottom plate portion 22 is in contact at one location with an edge portion 43e of the vibration surface 43 in this example, for positioning. The replacement member 20 is supported by the horn vibrator 40 and an element (not shown) of the main body 10, in a state of being slightly inclined with respect to the vibration surface 43. Note that the mesh portion 21a may be include a structure including many minute through holes in a flat plate instead of the film 21.

During operation of the mesh nebulizer 1, the user slightly tilts the main body 10 with respect to the vertical direction. Accordingly, liquid (in this example, medicinal liquid) is supplied from a liquid supply portion 17 in the main body 10 onto the vibration surface 43 of the horn vibrator 40 as indicated by arrow F. In other words, the medicinal liquid is supplied between the vibration surface 43 and the mesh portion 21*a*. Then, when the user switches on the power source switch, the drive voltage is applied to the piezoelectric element 41 of the horn vibrator 40 and the vibration surface 43 is vibrated via the horn 42. Accordingly, the medicinal liquid is nebulized through the mesh portion 21*a* (more accurately, through the multiple through holes penetrating through the film 21) and is sprayed through the opening 18.

FIG. 1 shows a block configuration of the ultrasonic vibrator driving apparatus 60 mounted in the mesh nebulizer 1.

The ultrasonic vibrator driving apparatus 60 includes a drive voltage generator 62 that generates a drive voltage (alternating voltage) to be applied to the horn vibrator 40 (more accurately, the piezoelectric element 41), a current detector 65 that detects the current flowing in the horn vibrator 40, and a controller 61 that controls the above-described drive voltage generator 62. Reference numeral 69 indicates grounding (GND).

The drive voltage generator 62 includes a variable frequency oscillator 63 and an amplifier 64. The variable frequency oscillator 63 includes a commercially-available function generator IC (integrated circuit), for example, and generates a square-wave alternating voltage that is to be the origin of the drive voltage, with a variable frequency within a frequency range including the resonance frequency fr of the horn vibrator 40. In this example, the variable frequency oscillator 63 includes a function according to which it is possible to vary the frequency by about 0.05 kHz at a time, within a range of at least about 175 kHz to about 185 kHz. Also, the ratio between the positive voltage period and the negative voltage period of the alternating voltage is variable, but in this example, it is 1 to 1 (e.g., about 50% duty). The amplifier 64 amplifies the alternating voltage generated by the variable frequency oscillator 63 and outputs a drive voltage having sufficient amplification for driving the horn vibrator 40.

The current detector 65 includes a resistance element (not shown) for current detection, for example, and an operational amplifier (not shown) that amplifies the voltage that dropped in the resistance element, and outputs the current that is to flow in the horn vibrator 40. In this example, the current detector 65 is used only to set a later-described reference frequency fo before the start of driving of the horn vibrator 40 and is not used during driving.

The controller 61 includes a CPU (Central Processing Unit), controls the operation of the drive voltage generator 62 by functioning as a sweep controller, and controls the overall operation of the mesh nebulizer 1.

As described with reference to FIGS. 8 and 9, when the frequency f of the drive voltage is slightly lower than the resonance frequency fr of the horn vibrator 40, the horn vibrator 40 vibrates efficiently, whereas if the frequency f of the drive voltage slightly exceeds the resonance frequency fr of the horn vibrator 40, the horn vibrator 40 substantially stops vibrating. Also, as described with reference to FIG. 11, if the temperature of the horn vibrator 40 and its surroundings increases, the resonance frequency fr of the horn vibrator 40 decreases, whereas if the temperature of the horn vibrator 40 and its surroundings decreases, the resonance frequency fr of the horn vibrator 40 increases.

In view of this, in this mesh nebulizer 1, the controller 61 performs the processing shown in FIG. 3 to stably drive the horn vibrator 40, regardless of the manufacturing variation and temperature dependency of the resonance frequency.

Specifically, when the power source switch of the mesh nebulizer 1 is switched on, before the start of the nebulization operation (the operation of the horn vibrator 40), in step S11 of FIG. 3, the controller 61 functions as a reference frequency setter to perform the following processing to set the reference frequency.

That is, as shown in FIG. 4, the controller 61 sequentially changes the frequency f of the drive voltage generated by the drive voltage generator 62 (more accurately, the variable frequency oscillator 63) by about 0.2 kHz at a time in a range of about 175 kHz to about 185 kHz in this example. Here, the range in which the frequency f=about 175 kHz to about 185 kHz is a range in which it is expected that the resonance frequency fr of the horn vibrator 40 mounted on the main body 10 is definitely included, considering the manufacturing variation and temperature dependency of the resonance frequency. In addition, the controller 61 receives the output of the current detector 65 and sequentially samples and inputs the current value (effective value) of the current flowing in the horn vibrator 40. Furthermore, the controller 61 divides the voltage value (effective value) Ve of the drive voltage by the current value Ie to obtain the minimum value Zmin of the impedance Z of the horn vibrator 40 in the range in which the frequency f of the drive voltage is about 175 kHz to about 185 kHz, for example. Also, the frequency f when the minimum value Zmin is obtained is recognized as being the resonance frequency fr of the horn vibrator 40. In this manner, the controller 61 searches for and obtains the resonance frequency fr. Also, in this example, the reference frequency fo is set according to the obtained resonance frequency fr, so as to match the resonance frequency fr. That is, it is set such that fo=fr.

Accordingly, even if the resonance frequencies fr of the individual horn vibrators 40 differ due to the manufacturing variation and temperature dependency of the horn vibrator 40, the reference frequency fo is able to be set appropriately according to the resonance frequencies fr of the individual horn vibrators 40.

Note that in this example, the reference frequency fo is set so as to match the obtained resonance frequency fr, but there is no limitation to this. The controller 61 may also set the reference frequency fo to be slightly lower, for example, about 0.2 kHz lower than the obtained resonance frequency fr.

Next, in step S12 of FIG. 3, the controller 61 functions as the sweep controller to control the frequency f of the drive voltage as described in (1) and (2) below.

(1) Essentially, as shown in FIG. 5A, the controller 61 repeatedly sweeps the frequency f of the drive voltage by predetermined sweep widths Δf1 and Δf2 and a predetermined sweep period ΔS so as to include the resonance frequency fr, based on the reference frequency fo set according to the resonance frequency fr of the horn vibrator 40. Here, Δf1=Δf2>0 is set. In this example, in one sweep period ΔS, the frequency f of the drive voltage increases from the reference frequency fo to (fo+Δf1) toward the side of exceeding the reference frequency fo as time t elapses, and thereafter, the frequency f of the drive voltage linearly decreases to (fo−Δf2) toward the side of being less than the reference frequency fo, via the reference frequency fo, and furthermore linearly increases and returns to the reference frequency fo. FIG. 5B corresponds to FIG. 5A, and schematically shows a manner in which the drive voltage V changes accompanying the elapse of time t.

In this manner, the controller 61 repeatedly sweeps the frequency f of the drive voltage with the predetermined sweep widths Δf1 and Δf2 and the predetermined sweep period ΔS so as to include the resonance frequency fr, based on the reference frequency fo set according to the resonance frequency fr of the horn vibrator 40. For example, at the time of starting operation, when the frequency f of the drive voltage is slightly (e.g., about 0.2 kHz) lower than the resonance frequency fr of the horn vibrator 40, the horn vibrator 40 vibrates efficiently. Accordingly, the temperature T of the horn vibrator 40 and its surroundings increases as indicated by arrow P1 in FIG. 7. When the temperature T of the horn vibrator 40 and its surroundings increases, the resonance frequency fr of the horn vibrator 40 decreases as indicated by the arrow P2 in FIG. 7. Accordingly, compared to the state at the time of starting operation, the period in the sweep period ΔS in which the frequency f of the drive voltage exceeds the resonance frequency fr of the horn vibrator 40 becomes longer, and the period of the sweep period ΔS in which the horn vibrator 40 substantially does not vibrate becomes longer. Accordingly, the temperature T of the horn vibrator 40 and its surroundings decreases as indicated by the arrow P3 in FIG. 7. When the temperature T of the horn vibrator 40 and its surroundings decreases, the resonance frequency fr of the horn vibrator 40 increases as indicated by the arrow P4 in FIG. 7. Accordingly, compared to the immediately prior state, the period in the sweep period ΔS in which the frequency f of the drive voltage is less than the resonance frequency fr of the horn vibrator 40 becomes longer, and the period of the sweep period ΔS in which the horn vibrator 40 efficiently vibrates becomes longer. Accordingly, the temperature T of the horn vibrator 40 and its surroundings increases once again as indicated by arrow P1 in FIG. 7. In this manner, the temperature change of the horn vibrator 40 and its surroundings is substantially feedback-controlled and suppressed or prevented. As a result, the horn vibrator 40 is stably driven, regardless of the temperature dependency of the resonance frequency fr of the horn vibrator 40. Also, since the sweeping is performed based on the reference frequency fo set according to the resonance frequency fr of the horn vibrator 40, the horn vibrator 40 is driven stably, regardless of the manufacturing variation of the resonance frequency fr of the horn vibrator 40.

Figure 5A:
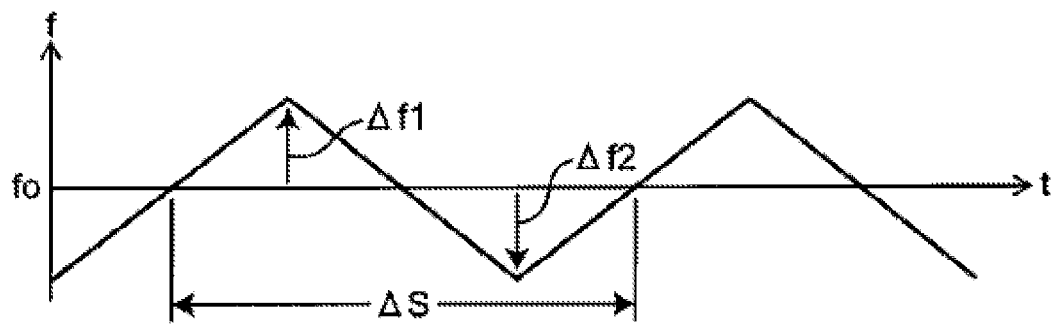
FIG. 5A is a time-frequency (t-f) line diagram illustrating a manner in which a frequency f of a driving voltage is swept over time.
Figure 5B:
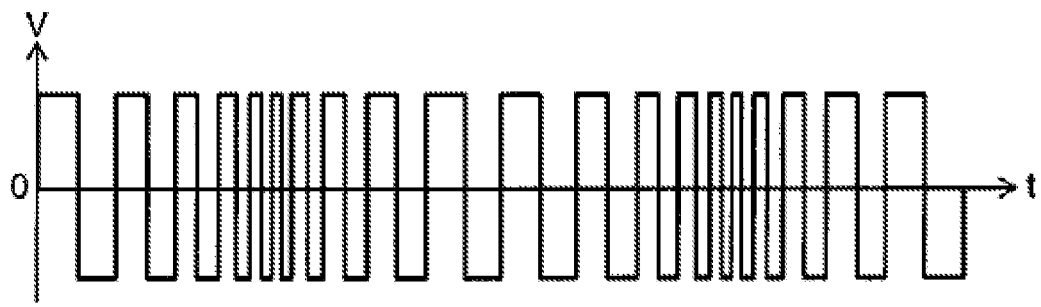
FIG. 5B corresponds to FIG. 5A, and is a time-voltage (t-V) line diagram schematically showing a manner in which the drive voltage changes over time.
Figure 5C:
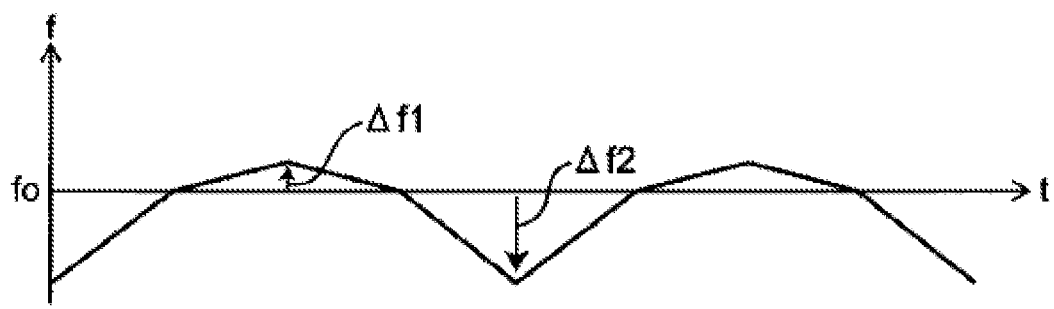
FIG. 5C is a time-frequency (t-f) line diagram illustrating another manner in which the frequency f of the drive voltage is swept over time.

Note that, as shown in FIG. 5C, the sweep width Δf1 of sweeping toward the side of exceeding the reference frequency fo may also be set to be smaller than the sweep width Δf2 of sweeping toward the side of being less than the reference frequency fo while the sweep width ΔS is kept constant. Accordingly, a period of the sweep period ΔS in which the horn vibrator 40 substantially does not vibrate is shorter than the period in which the horn vibrator 40 efficiently vibrates. Accordingly, reduction of the driving efficiency of the horn vibrator 40 is suppressed or prevented.

(2) Furthermore, the controller 61 associates and restricts the above-described sweep period ΔS and the sweep widths Δf1 and Δf2 for the frequency f of the drive voltage.

Figures 6, 7:
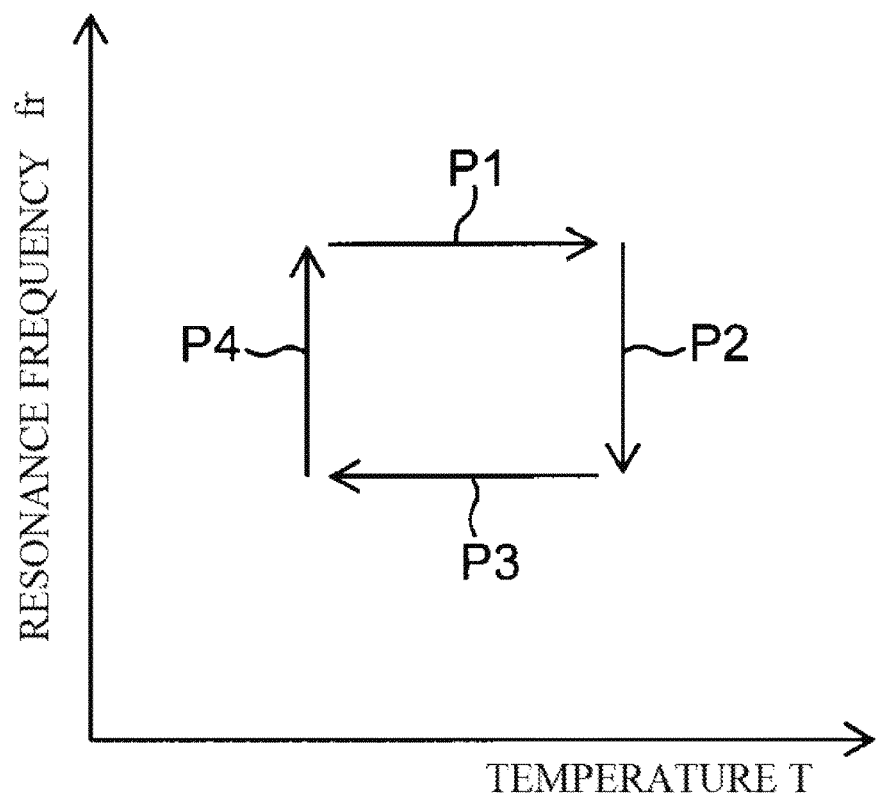
FIG. 6 is a diagram showing an allowed range A for sweep periods and sweep widths in a table serving as a two-dimensional map divided by the sweep periods and the sweep widths.
FIG. 7 is a diagram schematically showing how change in temperature of a horn vibrator and its surroundings is feedback-controlled.
Figure 8:
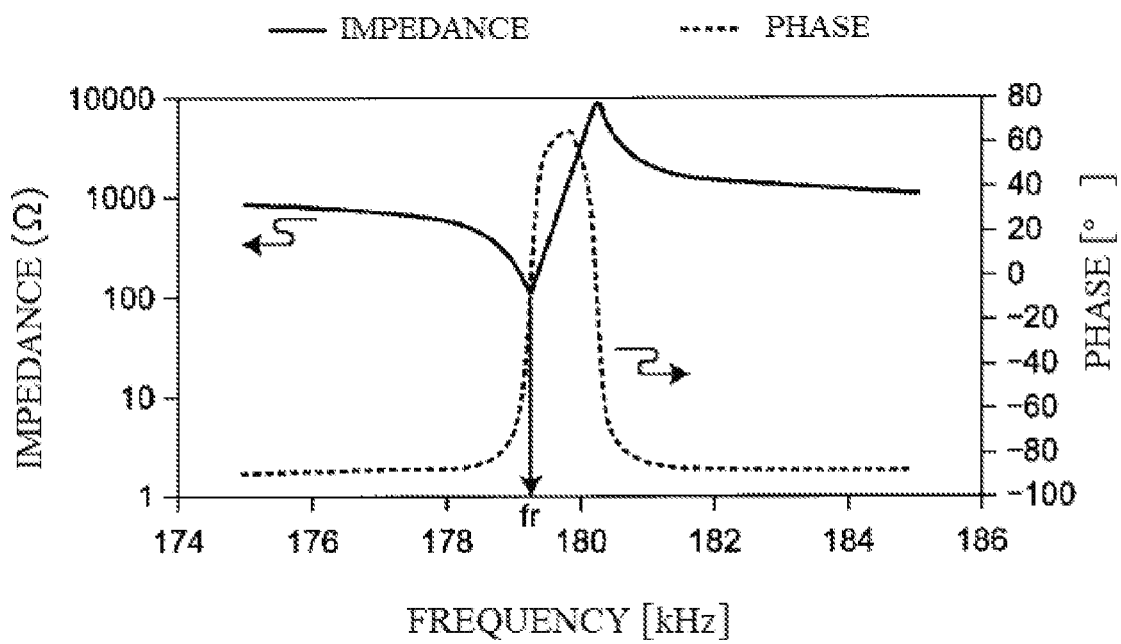
FIG. 8 is a diagram showing changes in impedance (indicated by a solid line) and phase (indicated by a broken line) of the horn vibrator accompanying a change in the frequency of the drive voltage.
Figure 9:
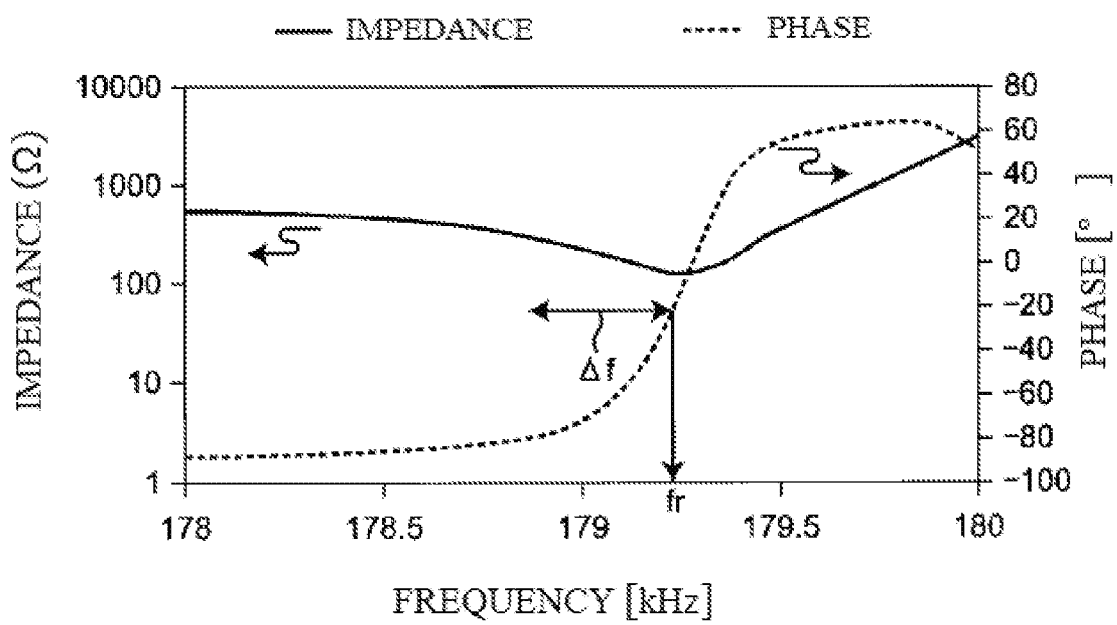
Figure 10:
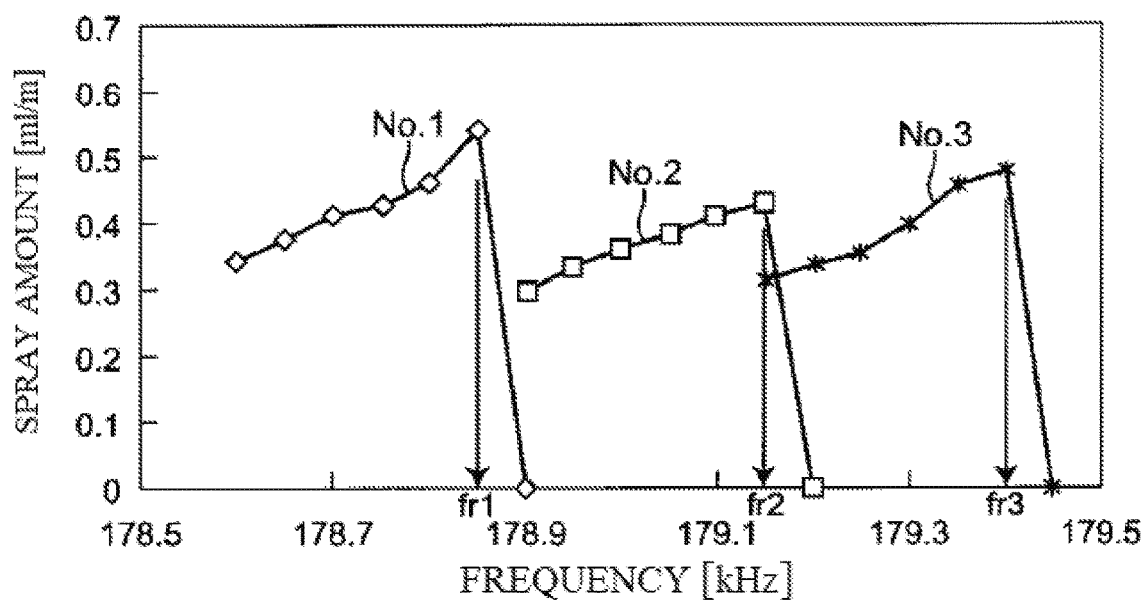
Figure 11:
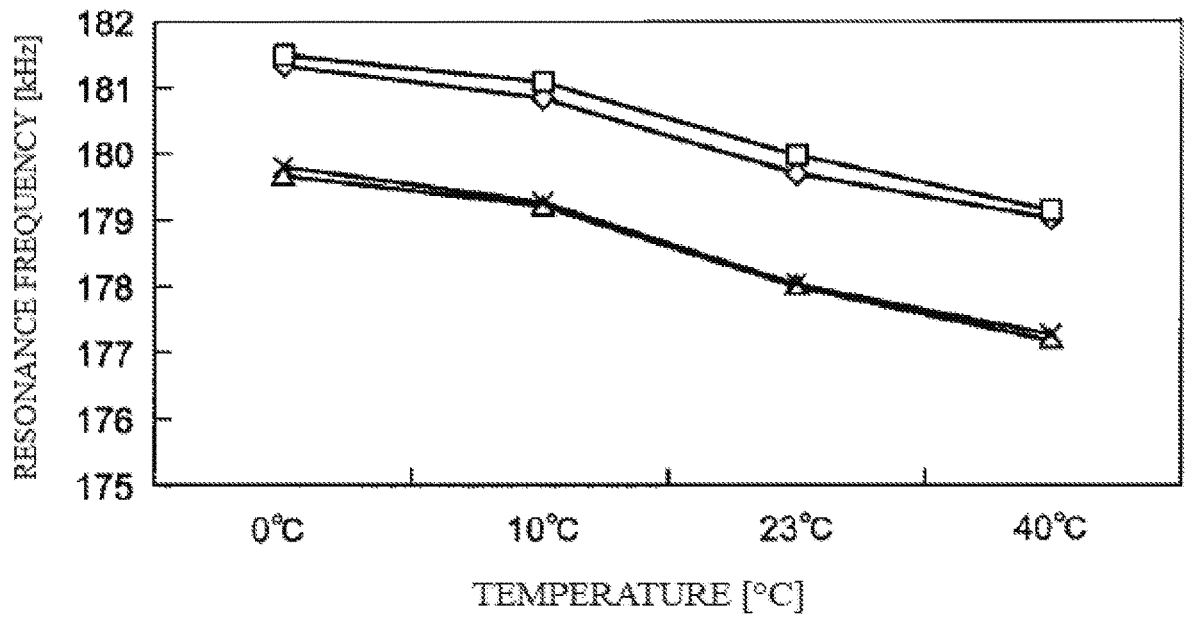

Specifically, FIG. 6 shows an allowed region (denoted by diagonal lines) A for the sweep frequency ΔS and the sweep widths Δf1 and Δf2 in a table serving as a two-dimensional map divided by the sweep period and the sweep width. The table head (top row) of the table shown in FIG. 6 shows the divisions for the sweep period ΔS. In this example, the sweep period ΔS is divided into four divisions, namely about 0.05 msec, about 0.1 msec, about 1 sec, and about 10 sec. The table side (left column) of the table shown in FIG. 6 shows the divisions for the sweep widths Δf1 and Δf2. In this example, the sweep widths Δf1 and Δf2 are divided into five divisions with the following approximate values, namely "fo±0.75 kHz", which indicates that Δf1=Δf2=0.75 kHz, "fo±0.5 kHz", which indicates that Δf1=Δf2=0.5 kHz, "fo±0.25 kHz", which indicates that Δf1=Δf2=0.25 kHz, "fo±0.1 kHz", which indicates that Δf1=Δf2=0.1 kHz, and "fo-0.25 kHz to fo+0.1 kHz", which indicates that Δf1=0.1 kHz and Δf2=0.25 kHz. The ○ marks in the body of the table shown in FIG. 6 indicate that the spray amount of the medicinal liquid is about 90% or more of the spray amount (in this example, about 0.5 ml/m) when the horn vibrator 40 is vibrated at the resonance frequency fr in the divisions denoted by that mark. On the other hand, the x marks indicate that the spray amount of the medicinal liquid is less than about 90% of the spray amount achieved when the horn vibrator 40 is vibrated at the resonance frequency fr in the divisions denoted by that mark. For example, in the case where the sweep period ΔS=about 0.05 msec, if the sweep width Δf1=Δf2=about 0.74 kHz, the ○ mark is used, and if Δf1=Δf2=about 0.76 kHz, the x mark is used. On the other hand, in the case where the sweep width Δf1=Δf2=about 0.5 kHz, if the sweep period ΔS=about 0.09 msec, the ○ mark is used, and if the sweep period ΔS=about 1.1 msec, the x mark is used. The boundary Ao between the allowed region A denoted by the ○ marks and the non-allowed region B denoted by the x marks was first confirmed through an experiment conducted by the inventors of preferred embodiments of the present invention. Note that in the division "fo-0.25 kHz to fo+0.1 kHz", indicating that the sweep width Δf1=about 0.1 kHz and Δf2=about 0.25 kHz, the upper limit of the sweep period ΔS is greater than about 10 sec, which is extremely long, and therefore the upper limit of the sweep period ΔS was not confirmed.

In view of this, regarding the frequency f of the drive voltage, the controller 61 controls the sweep period ΔS and the sweep widths Δf1 and Δf2 such that they fall within the allowed range A of the table shown in FIG. 6. For example, the sweep period ΔS is set to about 10 sec, the sweep width Δf1 is set to about 0.1 kHz, and the sweep width Δf2 is set to about 0.25 kHz. Accordingly, reduction of the driving efficiency of the horn vibrator 40 can be reliably suppressed or prevented. In this example, the spray amount of the medicinal liquid is about 90% or more of the spray amount achieved when the horn vibrator 40 is vibrated at the resonance frequency fr.

Figure 3:
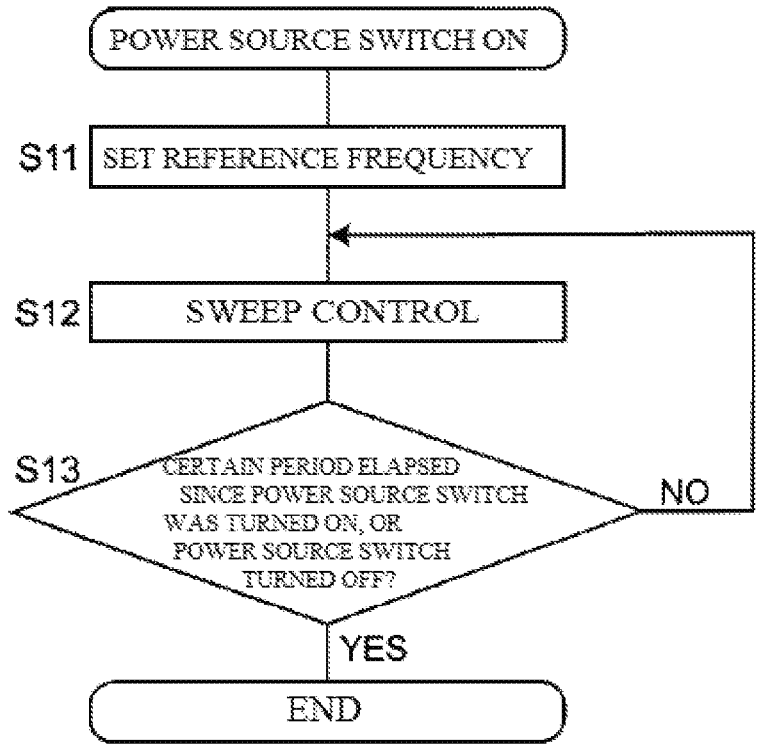
FIG. 3 is a diagram showing a flow of control for a controller included in the ultrasonic vibrator driving apparatus.
Figure 4:
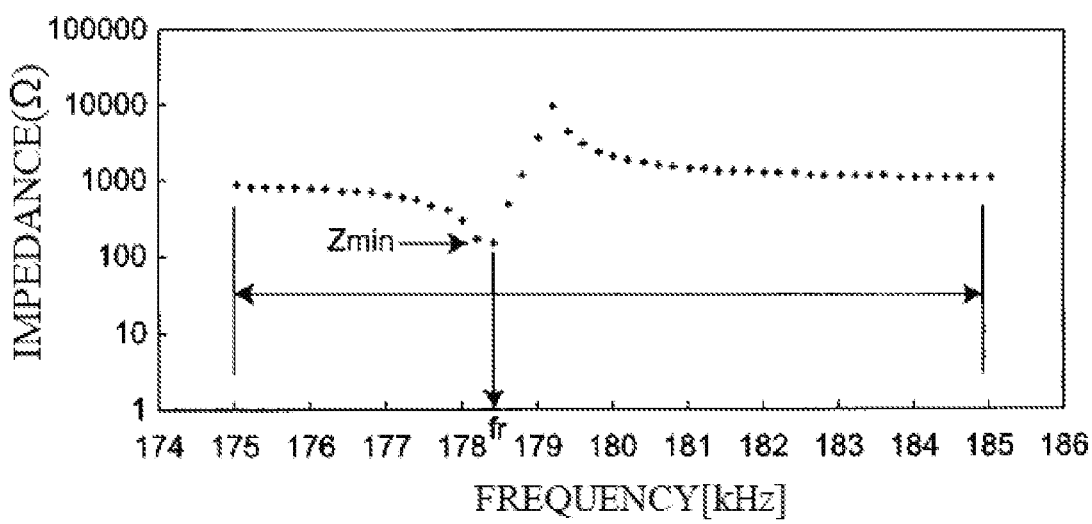
FIG. 4 is a diagram for illustrating processing for setting a reference frequency in the ultrasonic vibrator driving apparatus.

During the nebulization operation, the controller 61 does not return to step S11 in FIG. 3, but continues the control (step S12 in FIG. 3) of the frequency f of the drive voltage in (1) and (2) above. Accordingly, the nebulization operation is not interrupted in order to obtain the resonance frequency fr and the user is not made to wait. Thereafter, in step S13 of FIG. 3, when a certain period (e.g., about 10 minutes) has elapsed since the user switched on the power source switch, or when the user switches off the power source switch, the controller 61 ends the processing.

In this manner, with the mesh nebulizer 1 including the ultrasonic vibrator driving apparatus 60, the horn vibrator 40 accompanying the manufacturing variation and the temperature dependency of the resonance frequency is able to be driven stably while suppressing or preventing reduction of the driving efficiency. As a result, the medicinal liquid is able to be effectively nebulized and sprayed.

In the above example, as shown in FIG. 6, the "two-dimensional map" preferably is a two-dimensional table with four divisions for the sweep period and five divisions for the sweep width, for example, but there is no limitation to this. There may also be fewer divisions for the sweep period and for the sweep width. Conversely, it is also possible to use a two-dimensional graph in which the divisions for the sweep period ΔS and the sweep widths Δf1 and Δf2 are very small, and thus the boundary Ao between the allowed region A and the non-allowed region B is substantially smooth. This kind of "two-dimensional map" is preferably stored in a storage or memory (not shown) included in the controller 61.

Also, in the above example, as shown in FIGS. 5A and 5C, the frequency f of the driving voltage was increased and reduced linearly accompanying the elapse of time t, but there is no limitation to this. The frequency f of the drive voltage may also be swept in a curved manner, so as to draw a sine wave accompanying the elapse of time, for example.

Also, in the above example, the ultrasonic vibrator was the horn vibrator 40, but there is no limitation to this. Preferred embodiments of the present invention can also be applied to an ultrasonic vibrator that does not include a horn and includes a piezoelectric element.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An ultrasonic vibrator driving apparatus that operates by applying an alternating voltage as a drive voltage to an ultrasonic vibrator that includes a piezoelectric element and has a unique resonance frequency, the ultrasonic vibrator driving apparatus comprising:
    a drive voltage generator to generate the drive voltage with a variable frequency in a frequency range including the resonance frequency of the ultrasonic vibrator; and
    a sweep controller to repeatedly sweep the frequency of the drive voltage with a predetermined sweep width and a predetermined sweep period so as to include the resonance frequency, based on a reference frequency set according to the resonance frequency of the ultrasonic vibrator, and to associate and restrict the sweep period and the sweep width such that the sweep period and the sweep width fall within a predetermined allowed region on a two-dimensional map divided by the sweep period and the sweep width.

2. The ultrasonic vibrator driving apparatus according to claim 1, further comprising a reference frequency setter to search for and obtain the resonance frequency of the ultrasonic vibrator by sweeping the frequency of the drive voltage before a start of operation of the ultrasonic vibrator, and to set the reference frequency according to the obtained resonance frequency.

3. The ultrasonic vibrator driving apparatus according to claim 1, wherein the ultrasonic vibrator is a horn vibrator defined by an integral structure including the piezoelectric element and a horn to transmit vibration of the piezoelectric element.

4. A mesh nebulizer comprising:
    the ultrasonic vibrator driving apparatus according to claim 3; and
    a flat plate-shaped or sheet-shaped mesh portion facing a vibration surface of the horn vibrator; wherein
    a medicinal liquid supplied between the vibration surface and the mesh portion is nebulized and sprayed through the mesh portion.

5. The ultrasonic vibrator driving apparatus according to claim 1, wherein
    the vibration of the ultrasonic vibrator is used to nebulize and spray a medicinal liquid; and
    the allowed region on the two-dimensional map is set such that a spray amount of the medicinal liquid is about 90% or more of a spray amount achieved when the ultrasonic vibrator is vibrated at the resonance frequency.

6. The ultrasonic vibrator driving apparatus according to claim 1, wherein the sweep controller sets the sweep width to sweep toward a side of exceeding the reference frequency to be smaller than the sweep width to sweep toward a side of being less than the reference frequency, while keeping the sweep period constant.

7. The ultrasonic vibrator driving apparatus according to claim 6, wherein the sweep controller sets the sweep width to sweep toward the side of exceeding the reference frequency to about 0.10 kHz and the sweep width to sweep toward the side of being less than the reference frequency to about 0.25 kHz, while keeping the sweep period constant.

* * * * *